United States Patent [19]

Homeier et al.

[11] 3,939,213

[45] Feb. 17, 1976

[54] PREPARATION OF POLYALKOXYALKYL COMPOUNDS

[75] Inventors: Edwin H. Homeier, Maywood; Robert A. Dombro, Arlington Heights, both of Ill.

[73] Assignee: Universal Oil Products Company, Des Plaines, Ill.

[22] Filed: May 20, 1974

[21] Appl. No.: 471,515

[52] U.S. Cl. ...... 260/615 B; 260/611 B; 260/611 A; 260/615 R
[51] Int. Cl.² .................... C07C 41/02; C07C 41/06
[58] Field of Search.......... 260/615 B, 611 B, 615 R

[56] References Cited
UNITED STATES PATENTS

| | | | |
|---|---|---|---|
| 3,294,848 | 12/1966 | Earing et al. | 260/615 B |
| 3,419,505 | 12/1968 | Marsico | 260/615 B |
| 3,450,647 | 6/1969 | Gunther et al. | 260/611 BY |
| 3,703,483 | 11/1972 | Bozik et al. | 260/615 B |

OTHER PUBLICATIONS

Sawdno et al., Chem. Abs., 77, C1972 74826k.

*Primary Examiner*—Howard T. Mars
*Attorney, Agent, or Firm*—James R. Hoatson, Jr.; Raymond H. Nelson; William H. Page II

[57] ABSTRACT

Polyalkoxyalkyl compounds are prepared from the treatment of an olefinic compound with an epoxide in an atmosphere of hydrogen in the presence of a catalyst comprising a transition metal-containing compound.

9 Claims, No Drawings

PREPARATION OF POLYALKOXYALKYL COMPOUNDS

This invention relates to a process for the preparation of polyalkoxyalkyl compounds. More specifically, this invention relates to a process for the preparation of polyalkoxyalkyl compounds which comprises the treatment of an olefinic compound with an epoxide in an atmosphere of hydrogen in the presence of a catalyst comprising a transition metal-containing compound at reaction conditions, and recovering the resultant polyalkoxyalkyl compound.

Processes directed to the preparation of surface-active agents or surfactants are well known in the art. For example, it is known that glycols or glycol ethers may be prepared by the epoxidation of a mixture of normal alpha olefins with an organic hydroperoxide in the presence of specific catalysts. The resulting 1,2-epoxides are reacted with water or ethylene glycol to form any desired corresponding glycols or glycol ethers. It is also well known in the art that an adduct of about 5 to about 75 weight percent of ethylene oxide and an aminoester may possess surface-active qualities.

In contradistinction to the prior art, it has now been shown that surface-active agents or nonionic surfactants may be prepared by the treatment of an olefinic compound with an epoxide in an atmosphere of hydrogen in the presence of a catalyst comprising a transition metal-containing compound and recovering the resultant nonionic surfactant, namely, the polyalkoxyalkyl compound.

The utilization of the above set forth invention will allow a one-step process for the production of the nonionic surfactants from olefinic raw materials, thus, eliminating any hydroformylation or oxidation processes of olefinic compounds to form alcohols and thereafter treating the resultant alcohols to form any polyalkoxyalkyl compound. The elimination of the hydroformylation or oxidation step of the olefin compounds will reduce the cost of manufacturing the polyalkoxyalkyl compounds and create a greater diversity within the nonionic surfactants as a result of the opportunity to utilize a greater complexity of starting material. For example, a manufacturer may now start with olefins possessing a range of carbon numbers, such as $C_{11}$ to $C_{14}$ olefins or $C_{15}$ to $C_{18}$ olefins without concern as to the carbon number of any requisite alcohol which results from any hydroformylation or oxidation intermediate step before the final production of the desired polyalkoxyalkyl compound.

The desired products of the process of this invention, namely, polyalkoxyalkyl compounds are utilized in the chemical industry in many ways. For example, polyalkoxyalkyl compounds are nomenclated as surface-active agents, (sometimes called nonionic surfactants) which are used in the chemical industry in synthetic detergents; in the textile industry in scouring, kier boiling, and other various steps to stabilize and prevent channeling of oil; as alkylarenesulfonate agents; lubricating oils; natural waxes and similar materials; in dye baths to aid penetration and act as leveling agents; in the metal cleaning industry; in ore filtration to modify the surface of the mineral selectivity as frothing agents; as insecticidal sprays, etc. A specific use of the polyalkoxyalkyl compounds is the use of polyalkoxylated tetradecane which may be used in detergents, as a wetting agent or to treat synthetic fibers.

It is therefore an object of this invention to provide a process for the preparation of polyalkoxyalkyl compounds.

A further object of this invention is to provide a process for the preparation of the polyalkoxyalkyl compounds using a specific catalytic composition of matter in order to produce a greater percentage of the polyalkoxyalkyl compounds in a more expedient manner.

In one aspect an embodiment of this invention resides in a process for the preparation of a polyalkoxyalkyl compound which comprises the treatment of an olefinic compound with an epoxide in an atmosphere of hydrogen in the presence of a catalyst comprising a transition metal-containing compound at reaction conditions, and recovering the resultant polyalkoxyalkyl compound.

A specific embodiment of this invention resides in a process for the treatment of decene-5 with ethylene oxide in an atmosphere of hydrogen comprising a pressure of 80 atmospheres and a catalyst comprising $\pi$-cyclopentyldienyltitanium trichloride at a temperature of about 100°C. to about 300°C., and recovering the resultant polyalkoxyalkyl compound, namely, polyalkoxylated decane.

A second specific embodiment of this invention resides in a process for the treatment of tetradecene-7 with ethylene oxide in an atmosphere of hydrogen comprising 80 atmospheres in the presence of a catalyst comprising bis($\pi$-cyclopentyldienyl)titanium oxide at a temperature of 150°C. and recovering the resultant polyalkoxyalkyl compound, namely, polyalkoxylated tetradecane.

Other objects and embodiments will be found in the following further detailed description of the present invention.

As hereinbefore set forth the present invention is concerned with a process for the preparation of polyalkoxyalkyl compounds which comprises the treatment of an olefinic compound with an epoxide in an atmosphere of hydrogen in the presence of a catalyst comprising a transition metal-containing compound. The polyalkoxylation is effected under reaction conditions which include a temperature in the range of from about 100°C to about 500°C. In addition, another reaction condition involves pressure, said pressure ranging from atmospheric up to 100 atmospheres or more. When superatmospheric pressure is employed said pressure is afforded by the introduction of the hydrogen gas which is present during the reaction or if so desired the pressure is partially afforded by the hydrogen gas while the remaining partial pressure is afforded by a substantially inert gas such as nitrogen, helium, argon, etc. Another variable which is employed is the amount of reactants, the olefin being present in a mol ratio in the range of from about 1 mol of olefin per 1 mol of epoxide to about 1 mol of olefin per 100 mols of the ethylene oxide.

Examples of suitable ethylene oxide compounds which are utilized as one of the starting materials in the ethoxylation process of this invention would include, in particular all those epoxides which would be in accordance with Formula 1

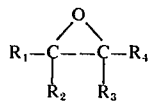

FORMULA I wherein $R_1$, $R_2$, $R_3$, or $R_4$ is selected from the group consisting of hydrogen, lower alkyl possessing between about 1 to about 6 carbon atoms, lower cycloalkyl, aryl, cycloalkylaryl, alkaryl, aralkyl, such as ethylene oxide, propylene oxide, 1,4-butylene oxide, 2,3-dimethyl-1,4-butylene oxide, cyclohexylethylene oxide, 1,1-dicyclohexylethylene oxide, 1,2-dicyclohexylethylene oxide, phenylethylene oxide, 1,1-diphenylethylene oxide, 1,2-diphenylethylene oxide, (2-cyclohexylphenyl)ethylene oxide, (2-cyclopentylphenyl)ethylene oxide, (2-methylphenyl)ethylene oxide, (also known as 2-tolylethylene oxide), 1-phenyl-1,4-butylene oxide, 1,4-(di-2-tolyl)-2,3-butylene oxide, 2,3-(1-benzyl)propylene oxide, etc.

Examples of suitable olefinic compounds which may be used to treat the ethylene oxide in the process of this invention would include, in particular, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, heptene-1, nonene-1, decene-1, 3-methylheptene-1, 2-methylheptene-2, nonene-3, 3-methyloctene-2, decene-2, decene-5, decene-4, decene-3, 3,4-dimethyloctene-2, 4-ethyloctene-2, undecene-3, undecene-4, undecene-2, undecene-1, undecene-5, 4-methyldecene-2, 4,5-dimethylnonene-2, dodecene-1, dodecene-2, dodecene-3, dodecene-4, dodecene-5, tridecene-1, tridecene-2, tridecene-3, tetradecene-2, tetradecene-3, tetradecene-1, tetradecene-4, tetradecene-5, tetradecene-6, tetradecene-7, pentadecene-4, pentadecene-5, pentadecene-6, pentadecene-1, hexadecene-1, heptadecene-1, heptadecene-2, heptadecene-3, 2-methoxybutene-2, 2-methoxypentene-1, 2-methoxyhexene-1, 1-propoxyheptene-1, 2-diethoxyoctene-1, 2,3-diethoxyundecene-3, 1-chlorobutene-2, 2-chloropentene-1, 2-bromohexene-2, 2,3-dichlorooctene-1, 3-iodooctene-2, 2-methoxy-3-chlorodecene-2, 3,4-dimethyl-2-chlorooctene-2, or mixtures of linear internal and terminal olefins such as internal olefins possessing carbon numbers between 11 and 14 or 15 and 18. It is understood that the aforementioned epoxides and olefins are only representative of the class of ocmpounds which may be employed and that the present invention is not necessarily limited thereto.

The catalytic composition of matter which is used in the process of this invention includes a transition metal-containing compound. The term "transition metal" used in the specification and appended claims being defined as a metal selected from the group consisting of Group IB, IIB, IIIB, IVB, VB, VIB, VIIB, and Group VIII of the Periodic Table. Suitable examples of compounds containing transition metals which may be utilized as catalysts in the process of this invention would include copper chloride, silver chloride, gold acetate, zinc chloride, cadmium acetate, mercuric chloride, scandmium chloride, yttrium hydroxide, π-cyclopentadienyltitanium trichloride, bis(π-cyclopentyldienyltitanium)oxide, bis(π-cyclopentadienyltitanium)dichloride, π-cyclopentadienylzirconium trichloride, π-cyclopentadienylhafnium oxide, vanadium trichloride, neobium trichloride, tantallium trichloride, chromium trichloride, molybdenum trichloride, π-cyclopentadienyltungsten trichloride, manganese acetate, technetium decacarbonyl, dirhenium decacarbonyl, ferric chloride, cobalt acetate, palladium acetate, nickel acetate, rhodium acetate, ruthenium hydroxide, diosmium decacarbonyl, iridium acetate, platinum acetate, etc. It is also contemplated within the scope of this invention that any combination of the transition metals may be used in conjunction with each other as catalysts fr the polyalkoxylation process although not necessarily with equivalent results. It is understood that the aforementioned catalysts comprising a transition metal-containing compound are only representative of the class of compounds which may be employed as catalysts and that the present invention is not necessarily limited to those catalysts herein set forth.

The process of this invention may be effected in any suitable manner and may comprise either a batch or continuous type operation. For example, when a batch type operation is employed, the reactant comprising the olefinic compound is placed in an appropriate apparatus along with a transition metal-containing compound catalyst. If atmospheric pressure is to be employed, the reaction vessel is equipped with a hydrogen source at the bottom of the vessel so as to create a flow of hydrogen gas through any reactants which may be involved. The epoxide may also be entered through the hydrogen entry device in conjunction with the hydrogen or it may be entered separately through a separate epoxide charge stream. Alternatively, if superatmospheric pressures are employed in the reaction the reactant comprising the olefinic compound and the catalyst comprising a transition metal-containing compound are charged to a pressure vessel such as a rotating autoclave. The rotating autoclave is sealed and hydrogen gas is pressed in until the desired operating pressure is attained. Epoxide is then charged to the reactant olefin whereby the polyalkoxylation will result. It should be noted that the epoxide may be charged through a separate reservoir to the autoclave or it may enter through the hydrogen stream to the treatment with the olefinic compound. The autoclave is then heated to the desired operating temperature and maintained thereat for a predetermined residence time and at the end of this time, the heating is discontinued, the autoclave is allowed to return to room temperature and excess pressure is discharged. The autoclave is opened and the reaction mixture is then treated to recover and separate the catalyst and any reactants from the desired polyalkoxyalkyl compound, said means of separation and recovery including washing, drying, extraction, evaporation, fractional distillation, etc.

It is also contemplated within the scope of this invention that the reaction process for obtaining the polyalkoxyalkyl compounds may be effected in a continuous manner of operation. When such a type of operation is employed, the reactants are continuously charged to a reaction vessel containing a transition metal-containing compound catalyst, said reaction vessel being maintained at proper operating conditions of temperature and hydrogen pressure. After completion of the desired residence time, the reactor effluent is continuously withdrawn and subjected to conventional means of separation whereby the desired polyalkoxyalkyl compound is recovered, while any unreacted starting materials comprising the olefinic compound or the ethylene oxide are recycled to the reaction zone to form a portion of the feedstock. Insofar as the catalytic composition of matter is solid in nature, various types of continuous operations may be used. One such type of operation comprises the fixed bed method in which the catalyst is disposed as a fixed bed in the reaction zone and the reactants are passed over said fixed bed in either an upward or downward flow. Another type of operation which may be employed comprises the moving bed type operation in which the catalyst and the reactants are passed through the reaction zone either concurrently or countercurrently to each or the slurry type operation in which the catalyst is carried into the reaction zone as a slurry in either or both of the reactants.

Examples of polyalkoxyalkyl compounds which may be prepared according to the process of this invention would include ethoxylated ethane, ethoxylated propane, ethoxylated butane, ethoxylated pentane, ethoxylated heptane, ethoxylated heptane, ethoxylated octane, ethoxylated nonane, ethoxylated decane, ethoxylated undecane, ethoxylated dodecane, ethoxylated tridecane, ethoxylated tetradecane, ethoxylated heptadecane, ethoxylated pentadecane, ethoxylated hexadecane, ethoxylated nonadecane, ethoxylated eicosane, propoxylated pentane, propoxylated decane, butoxylated heptadecane, pentoxylated octadecane, etc. It should be noted that the polyalkoxylation may take place at any carbon atom upon the olefin chain and it is contemplated within this invention that polyalkoxylation may take place in longer chained olefinic compounds. It is to be further understood that the aforementioned polyalkoxyalkyl compounds are only representative of the class of compounds which may be prepared and that the present invention is not necessarily limited thereto.

The following examples are given to illustrate the process of the present invention which, however, are not intended to limit the generally broad scope of the present invention in strict accordance therewith.

EXAMPLE I

In this example 143.0 mmoles of decene-5 was changed to an 850 milliliter glass-lined rotating autoclave along with 4.5 mmoles of $\pi$-cyclopentadienyltitanium trichloride. The autoclave was flushed to assure avoidance of any impurities by pressurizing with nitrogen and releasing the pressure, said procedure was repeated three separate times. A reservoir containing ethylene oxide gas was attached to the aforementioned rotating autoclave so as to afford a direct flow of ethylene oxide gas from the reservoir to the autoclave. A stream of hydrogen was charged between the reservoir of ethylene oxide and the autoclave, which contained decene-5 and $\pi$-cyclopentadienyltitanium trichloride, so as to provide a source of hydrogen and a carrier for the ethylene oxide gas to the rotating autoclave. Hydrogen and ethylene oxide were charged to the rotating autoclave until a pressure of 80 atmospheres had been effected within the autoclave. The quantity of ethylene oxide charged was measured by weighing the reservoir before and after charge, said quantity being determined as 364.0 mmoles of ethylene oxide. The autoclave was subsequently sealed and heated to a temperature of 150°C and maintained thereat for a period of time comprising 18 hours. After the passage of the 18 hour period of time the heating was terminated, the pressure released and the organic products were removed from the autoclave for analysis.

The organic products were analyzed by means of nuclear magnetic resonance spectroscopy, said spectrum of a $(CD_3)_2SO$ solution of the crude product disclosing the presence of the alkyl-moieties with pendant ethylene oxide groups thereby indicating an ethoxyalkyl compound and polyethylene oxide.

Polyethylene glycol and ethoxyalkyl components were separated by thin layer chromatography. The products were dissolved in benzene and eluted on a Carmagy Combination HVE and High Speed Chromatography Paper for a period of time comprising 17 hours. The elutant comprised the organic phase which was obtained by mixing one volume of glacial acetic acid, five volumes water and four volumes 1-butanol. The eluant was shaken and then aged for 24 hours before further analysis. A modified Draggendorf reagent was concocted as directed by Kirchner ed. in Weissenberg's, *Technique of Organic Chemistry-Volume XII, Thin Layer Chromatography*, Interscience, N.Y., 1967 at page 161. The characteristic colors obtained by spraying the chromatogram with the reagent and the $R_f$ values of the components were compared with those obtained with mixtures which were compounded from available samples of polyethylene oxide and polyethoxyalkyl compounds. This procedure definitely confirms the presence of the desired ethoxylated decane.

EXAMPLE II

In this example 102.0 mmoles of tetradecene-7 was charged to an 850 milliliter glass-lined rotating autoclave along with 10.3 mmoles of $\pi$-cyclopentadienyltitanium oxide. The autoclave was flushed to assure avoidance of impurities by pressurizing with nitrogen and releasing the pressure, said procedure was repeated three separate times. A reservoir containing ethylene oxide gas was attached to the aforementioned rotating autoclave so as to afford a direct flow of ethylene oxide gas from the reservoir to the autoclave. A stream of hydrogen was charged between the reservoir of ethylene oxide and the autoclave, which contained tetradecene-7 and $\pi$-cyclopentadienyltitanium oxide so as to provide a source of hydrogen and a carrier for the ethylene oxide gas to the rotating autoclave. Hydrogen and ethylene oxide were charged to the rotating autoclave until a pressure of 80 atmospheres had been effected within the autoclave. The quantity of ethylene oxide charged was measured by weighing the reservoir before and after entry, said quantity being determined as 455.0 mmoles of ethylene oxide. The autoclave was subsequently sealed and heated to a temperature of 150°C and maintained thereat for a period of time comprising 18 hours. After the passage of the 18 hour period of time, the heating was terminated, the pressure released and the organic products were removed from the autoclave for analysis.

The product recovered was analyzed as set forth in Example I above wherein it was determined that the desried product was a polyethoxylated tetradecane.

EXAMPLE III

In this example 157.0 mmoles of decene-5 was charged to an 850 milliliter glass-lined rotating autocalve along with 6.4 mmoles of vanadium trichloride. The autoclave was flushed to assure avoidance of impurities by pressurizing with nitrogen and releasing the pressure, said procedure was repeated three separate times. A reservoir containing ethylene oxide gas was attached to the aforementioned rotating autoclave so as to afford a direct flow of ethylene oxide gas from the reservoir to the autoclave. A separate stream of hydrogen was charged between the reservoir of the ethylene oxide and the autoclave, which contained decene-5 and vanadium trichloride, so as to provide a source of hydrogen and a carrier for the ethylene oxide gas to the rotating autoclave. Hydrogen and ethylene oxide were charged to the rotating autoclave until a pressure of 80 atmospheres had been effected within the autoclave. The quantity of ethylene oxide charged was measured by weighing the reservoir before and after entry, said quantity being determined as 455.0 mmoles of ethylene oxide. The autoclave was subsequently sealed and heated to a temperature of 150°C and maintained thereat for a period of time comprising 18 hours. After the passage of the 18 hour period of time, the heating was terminated, the pressure released and the organic products were removed from the autoclave for analysis.

The analysis of the recovered product was the same as that set forth in Example I above whereby it was disclosed that the product was shown to be polyethoxylated decane.

EXAMPLE IV

In this example 256.0 mmoles of decene-5 was charged to an 850 milliliter glass-lined rotating autoclave along with .01 mmoles of dirhenium decacarbonyl. The autoclave was flushed to assure avoidance of impurities by pressurizing with nitrogen and releasing the pressure, said procedure was repeated three separate times. A reservoir containing ethylene oxide gas was attached to the aforementioned rotating autoclave so as to afford a direct flow of ethylene oxide gas from the reservoir to the autoclave. A stream of hydrogen was charged between the reservoir of ethylene oxide and the autoclave, which contained decene-5 and dirhenium decacarbonyl so as to provide a source of hydrogen and a carrier for the ethylene oxide gas to the rotating autoclave. Hydrogen and ethylene oxide were charged to the rotating autoclave until a pressure of 80 atmospheres had been effected within the autoclave. The quantity of ethylene oxide charged was measured by weighing the reservoir before and after entry, said quantity being determined as 1700 mmoles of ethylene oxide. The autoclave was subsequently heated to a temperature of 150°C and maintained for a period of time comprising 18 hours. After passage of the 18 hour period of time, the heating was terminated, the pressure released and the organic products were removed from the autoclave for analysis.

The analysis of the products recovered was completed as set forth in Example I above, said analysis disclosed the presence of polyethoxylated decane.

EXAMPLE V

In this example 249.0 mmoles of decene-5 was charged to a 850 milliliter glass-lined rotating autoclave along with 4.5 mmoles of bis($\pi$-cyclopentadienyl)titanium dichloride, said contents of the autoclave being pretreated with 80 atmospheres of hydrogen pressure at 150°C for a period of time comprising 3 hours. A reservoir containing ethylene oxide gas was attached to the aforementioned rotating autoclave so as to afford a direct flow of ethylene oxide gas from the reservoir to the autoclave. A stream of ethylene oxide was charged to the autoclave, which contained decene-5, the hydrogen pressure and bis($\pi$-cyclopentadienyl)titanium dichloride. The quantity of ethylene oxide charged was measured by the weighing of the reservoir before and after entry, said quantity being determined as 2280.0 mmoles of ethylene oxide. The autoclave was subsequently sealed and heated to a temperature of 150°C and maintained thereat for a period of time comprising 16 hours. After the passage of the 16 hour period of time, the heating was terminated, the pressure released and the organic products were removed from the autoclave for analysis.

The products were analyzed as set forth in Example I above, said analysis disclosed the presence of polyethoxylated decane.

EXAMPLE VI

In this example heptene-3, chromium trichloride and propylene oxide are allowed to mix in a reaction vessel, said vessel being maintained at 450°C and a pressure of one atmosphere. Hydrogen gas is allowed to bubble-up through the reaction vessel but regulated so as to maintain a pressure of one atmosphere. The reactor effluent is recovered after a residence of two hours and the organic products are separated from any unreacted reactants which are recycled to form a portion of the charge stock.

The product is analyzed as set forth in Example I above, said analysis will disclose the product to be polypropoxylated heptane. This procedure is again repeated substituting butylene oxide for the propylene oxide, the final analysis disclosing the resultant product to be a butoxylated heptane.

We claim as our invention:

1. A process for the preparation of a polyalkoxylated alkane which comprises treating, at a temperature of about 100°C. to about 500°C. and a pressure of from 1 to about 100 atmospheres, an alkene having from 4 to 18 carbon atoms with ethylene oxide or propylene oxide in a hydrogen atmosphere in the presence of a catalyst selected from the group consisting of transition metal chlorides, hydroxides, acetates, and decacarbonyls and $\pi$-cyclopentadienyl derivatives of transition metal chlorides or oxides.

2. The process of claim 1 further characterized in that decene-5 is treated with ethylene oxide and the resultant polyalkoxyalkyl compound is a polyethoxylated decane.

3. The process of claim 1 further characterized in that heptene-3 is treated with propylene oxide and the resultant polyalkoxyalkyl compound is a polypropoxylated heptane.

4. The process of claim 1 further characterized in that tetradecene-7 is treated with ethylene oxide and the resultant polyalkoxyalkyl compound is a polyethoxylated tetradecane.

5. The process of claim 1 further characterized in that the catalyst comprising a transition metal-containing compound is $\pi$-cyclopentadienyltitanium trichloride.

6. The process of claim 1 further characterized in that the catalyst comprising a transition metal-containing compound is bis($\pi$-cyclopentadienyl)titanium oxide.

7. The process of claim 1 further characterized in that the catalyst comprising a transition metal-containing compound is vanadium trichloride.

8. The process of claim 1 further characterized in that the catalyst comprising a transition metal-containing compound is dirhenium decacarbonyl.

9. The process of claim 1 further characterized in that the catalyst comprising a transition metal-containing compound is chromium trichloride.

* * * * *